(12) United States Patent
Lai

(10) Patent No.: US 7,824,033 B2
(45) Date of Patent: Nov. 2, 2010

(54) APPARATUS AND METHOD FOR DETERMINING SPHERE AND CYLINDER COMPONENTS OF SUBJECTIVE REFRACTION USING OBJECTIVE WAVEFRONT MEASUREMENT

(75) Inventor: Shui T. Lai, Encinitas, CA (US)

(73) Assignee: Ophthonix, Inc., Vista, CA (US)

( * ) Notice: Subject to any disclaimer, the term of this patent is extended or adjusted under 35 U.S.C. 154(b) by 0 days.

(21) Appl. No.: 12/270,779

(22) Filed: Nov. 13, 2008

(65) Prior Publication Data

US 2009/0066915 A1 Mar. 12, 2009

Related U.S. Application Data

(62) Division of application No. 11/172,478, filed on Jun. 30, 2005, now Pat. No. 7,461,938.

(60) Provisional application No. 60/584,318, filed on Jun. 30, 2004.

(51) Int. Cl.
*A61B 3/10* (2006.01)
*A61B 3/02* (2006.01)

(52) U.S. Cl. .................. 351/205; 351/222; 351/241

(58) Field of Classification Search .................. 351/205, 351/210, 222–223, 237, 239, 241
See application file for complete search history.

(56) References Cited

U.S. PATENT DOCUMENTS

| 6,499,843 | B1 | 12/2002 | Cox et al. |
| 6,786,602 | B2 | 9/2004 | Abitbol |
| 2003/0151721 | A1 | 8/2003 | Lai et al. |
| 2003/0210378 | A1* | 11/2003 | Riza .......................... 351/205 |
| 2005/0057723 | A1 | 3/2005 | Wakil et al. |

OTHER PUBLICATIONS

Cheng et al., Journal of Vision (2004) 4:310-321.
MacRae et al., (eds.), "Customized Corneal Ablation The Quest For Super Vision," Slack Incorporated (2001), p. 37.
Thibos et al., Journal of Vision (2004) 4:329-351.

* cited by examiner

*Primary Examiner*—Scott J Sugarman
*Assistant Examiner*—Dawayne A Pinkney
(74) *Attorney, Agent, or Firm*—Morrison & Foerster LLP

(57) ABSTRACT

An apparatus for determining spherical and cylinder components of subjective refraction of a patient's vision includes a wavefront measurement device that can produce a measure of quality of vision in a return beam from the patient's eye viewing a target through a corrective test lens in the apparatus. The corrective lenses may be varied and a plurality of measurements of quality of vision may be obtained and analyzed to determine the spherical and cylinder components. Accordingly, the eye examiner may conduct a refraction examination without a subjective response from the patient.

15 Claims, 5 Drawing Sheets

APPARATUS AND METHOD FOR DETERMINING SPHERE AND CYLINDER COMPONENTS OF SUBJECTIVE REFRACTION USING OBJECTIVE WAVEFRONT MEASUREMENT

CROSS-REFERENCE TO RELATED APPLICATIONS

This application is a divisional application of U.S. Ser. No. 11/172,478, filed Jun. 30, 2005, which claims the benefit of priority under 35 U.S.C. §119(e) to U.S. Provisional Patent Application Ser. No. 60/584,318 entitled "Apparatus And Method For Determining Sphere And Cylinder Components Of Subjective Refraction Using Objective Wavefront Measurement," filed on Jun. 30, 2004, the contents of each of these applications are incorporated by reference herein in their entirety.

BACKGROUND OF THE INVENTION

1. Field of the Invention

The present invention relates generally to methods and apparatus for determining a person's visual characteristics, and more particularly to methods and apparatus for determining the sphere and cylinder components of a subjective refractive correction of the eye using objective wavefront measurement.

2. Description of the Related Art

Phoropters are apparatus used by optometrists to determine a patient's visual characteristics, so that proper eye diagnoses can be made and eyewear can be prescribed. In conventional phoropters, a patient views a target image through the phoropter, in which various test lenses are disposed, while an optometrist moves the test corrective lenses into the patient's field of view. The patient is then asked to verbally compare the quality of the perceived image as afforded by one lens versus another lens presented. The optometrist takes note of either an improvement or a deterioration in the patient's vision through such lenses. Systematically, the test progresses towards the "best" test lens entirely based on the patient's subjective responses. The lens parameters so determined are then used as the basis for a prescription for eyewear.

Unfortunately, as recognized herein, the patient can become fatigued during the process and/or misjudge the vision afforded by the various lenses. This can lead to the selection of a less than optimum prescription. Moreover, some patients, such as a very ill or a very young patient, might not be capable of articulating the quality of vision the various lenses afford the patient.

Objective refraction measurements using an auto-refractor are typically fast, require less operator skill and training, and are easier for a patient. However, because an auto-refractor typically does not measure subjective vision quality, it is not acceptable by the clinician as a replacement of subjective refraction measurements, and often an auto-refractor outcome is used as a starting point for subjective refraction measurement.

Wavefront sensing technology provides high degree of accuracy and is capable of capturing aberrations across the entire pupil in an instant. Many efforts have been made using wavefront data to predict a subjective refraction result. Thibos et. al. in "Accuracy and Precision of objective refraction from wavefront aberrations," published in the Journal of Vision 2004, vol. 4, pp. 329-351, tested 33 objective methods and found that the precision of these estimates is no better than 0.5 D within the 95% limit. It remains a challenge to be able to predict subjective refraction results using an objective measurement to the accuracy level of 0.25 D-0.35 D that offers clinician comfort and trust that such objective measurements can replace a manual phoropter.

Thus, what is needed are improved methods and apparatus for determining subjectively optimal refractive corrections of an eye based on objective measurements.

DETAILED DESCRIPTION OF THE PREFERRED EMBODIMENTS

One drawback of conventional objective measurement techniques is that generally no patient participation is involved other than offering an eye for the measurement process. In contrast, conventional subjective refraction measurement involves the patient making choices, and further involves consideration of visual optics, the neural pathway that connects optical sensors at the retina to the brain, the brain's processing and filtering, and finally a perception of an image. In conventional subjective refraction, an assessment of the image's quality is arrived at through this aggregate pathway. Embodiments of the present invention, however, make a connection between an objective wavefront measurement and a patient's response to a target inserted in their line-of-sight.

In particular, in embodiments disclosed herein, the subjective response of the patient can be objectively determined by monitoring fluctuations in the quality of vision as ascertained by objective wavefront measurements using a wavefront sensor. Reduced fluctuation is indicative of improved refractive correction. In one embodiment, fluctuations are monitored as different lenses (e.g., spherical and/or cylindrical) are placed in the field of view of the patient to test whether different types or amounts of correction improve vision.

Various systems and methods described herein advantageously enable quantification of the subjective response of the patient by performing objective measurements. By taking into account the subjective aspect of the patient's vision, a prescription for correction of refractive errors can be obtained. However, in preferred embodiments, instead of soliciting comments from the patient, for example, as optics in a phoropter are adjusted to evaluate the patient's vision, direct measurements from a wavefront sensor are used. In alternative embodiments described herein, not only can the spherical equivalent be determined from objective measurements of the wavefront, but subjective sphere, cylinder and axis values can be determined or estimated as well.

Discussion of methods for determining the spherical equivalent (SE) of the subjective refraction using an objective measurement is presented in U.S. patent application Ser. No. 10/076,218 entitled "Apparatus And Method For Determining Objective Refraction Using Wavefront Sensing," filed Feb. 13, 2002, as well as U.S. patent application Ser. No. 10/653,552, entitled "Apparatus And Method For Determining Subjective Responses Using Objective Characterization Of Vision Based On Wavefront Sensing" filed Sep. 2, 2003, both of which are hereby incorporated herein by reference in their entirety. Similar methods may be used to determine the cylinder and axis values as discussed more fully below.

Figure 1:
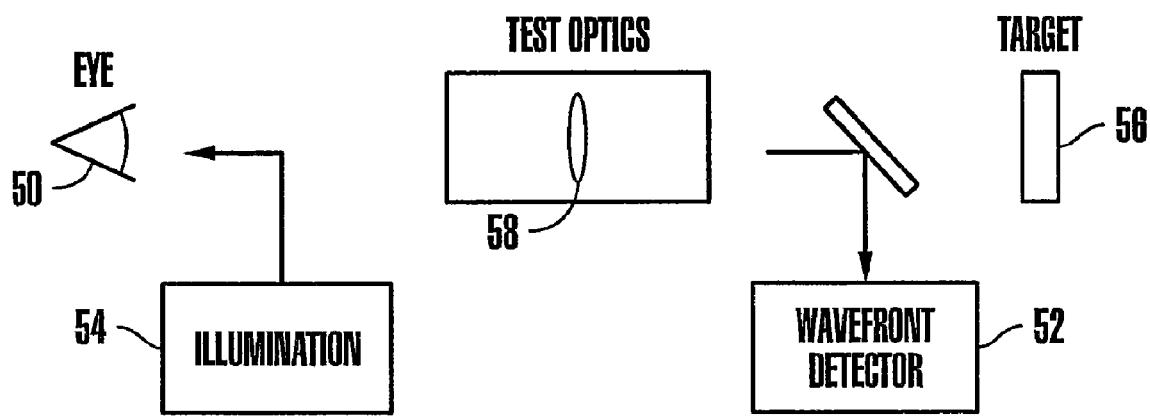
FIG. 1 is a schematic representation of one embodiment of a system for characterizing a patient's vision.

As illustrated in the non-limiting schematic diagram of FIG. 1, in a variety of approaches described herein, a determination of refractive correction of a patient's eye 50 may be achieved using a wavefront detector 52. Illumination 54 may be directed into the patient's eye 50 as the patient views a target 56 through a test lens 58 that may be varied or interchanged to provide different amounts of correction. A beamsplitter 53 permits the patient to view the target 56 while the patient's eye is simultaneously measured by the wavefront detector 52. Appropriate test lens correction is indicated by measurements from the wavefront detector 52.

A figure of merit such as a quality of vision metric may be computed based on a measurement performed by the wavefront sensor 52 on a wavefront emanating from the eye 50 as a result of illuminating the eye 50. In certain preferred embodiments, numerous measurements of the quality of vision metric are performed for each test lens value and the variation among these numerous measurements are calculated. This variation is illustrated by the error bars in the plot in FIG. 2 (discussed more fully below), which shows the quality of vision metric, represented by the quality of vision factor QVF, plotted for different test lens values. The units of measurement of QVF values will depend on the type of quality of vision metrics used (e.g., total root mean square (RMS) wavefront error, point-spread function, modulation transfer function, etc.) as discussed in further detail below. When an eye is at subjectively superior refractive correction, wavefront measurements typically display a reduced fluctuation. For example, in FIG. 2, the data point labeled 72 corresponds to the best objectively measured quality of vision. However the fluctuation associated with the data point labeled 74, as shown by the error bar, is smaller than that of data point 72, indicating that data point 74 corresponds to a superior subjective refraction. Accordingly, reduced or minimum variation may be correlated with the patent's subjective refraction. In this manner, this variation or fluctuation may be used to determine the refractive properties of the subject's eye 50 such as spherical equivalent (SE), as well as sphere, cylinder and axis. In various examples, for instance, to measure spherical equivalent values, figure of merit data together with variation of the figure of merit over N measurements are obtained and analyzed. The figure of merit data depends on which quality of vision metric is chosen as a measure of the quality of vision of the patient. In one example, the total RMS value of the wavefront error can be used as a measure of such quality of vision. These objective quantitative measurements, and in particular the extent of the variation of the figure of merit, manifest the subjective response of the patient as he or she reacts to various test lenses while viewing a target presented to the patient. When an eye is at subjectively optimum optical refractive correction, wavefront measurements typically exhibit reduced variation or fluctuation. Accordingly, knowledge of this fluctuation of a figure of merit of vision offers the ability of detecting subjective responses regarding the preferred refractive correction and thereby determining spherical equivalent. Additional details of an apparatus and method for obtaining variation of the figure of merit over repeated measurements of a variety of test lens values, in accordance with preferred embodiments of the invention, are more fully discussed below with reference to FIGS. 5-8. As used herein, the term "figure of merit" refers to any metric, parameter or value that may be measured or calculated that indicates or is related to quality of vision of a patient's eye.

In addition to determining spherical equivalent, however, such approaches may be employed to quantify the individual subjective refractive components of sphere, cylinder, and axis. The examiner is thereby able to determine the spherical and cylinder components of refraction (including axis) of the patient based on the objective measurements and also provide an eyeglass prescription.

One method for obtaining the cylinder and axis is to employ cylindrical test lenses. A series of cylindrical lenses can be introduced in the line-of-sight of the patient and multiple measurements of a figure of merit can be performed for each of the cylindrical test lenses. The fluctuation of the quality of vision can be compared using the same principle described above for determining the spherical equivalent. Without asking the patient which lens is preferred, the fluctuation of the patient's vision is measured. The lower the fluctuation the more preferable the cylindrical lens.

As a figure of merit in this example and various examples described herein, a quality of vision metric comprising the total RMS wavefront error of the patient's eye under examination may be employed. Other quality of vision metrics other than the total RMS wavefront error can also be used. These quality of vision metrics may include, but are not limited to, the point-spread function (PSF), the modulation transfer function (MTF), or the area integrated under the curve of the MTF. More quality of vision metrics can be found in a reference article by Cheng, Bradley, and Thibos, in Journal of Vision, 2004, vol. 4, pp. 310-321, which is incorporated herein by reference in its entirety. Virtually any of the quality of vision metrics can be chosen as the monitoring parameter for measuring vision fluctuation.

Figure 3:
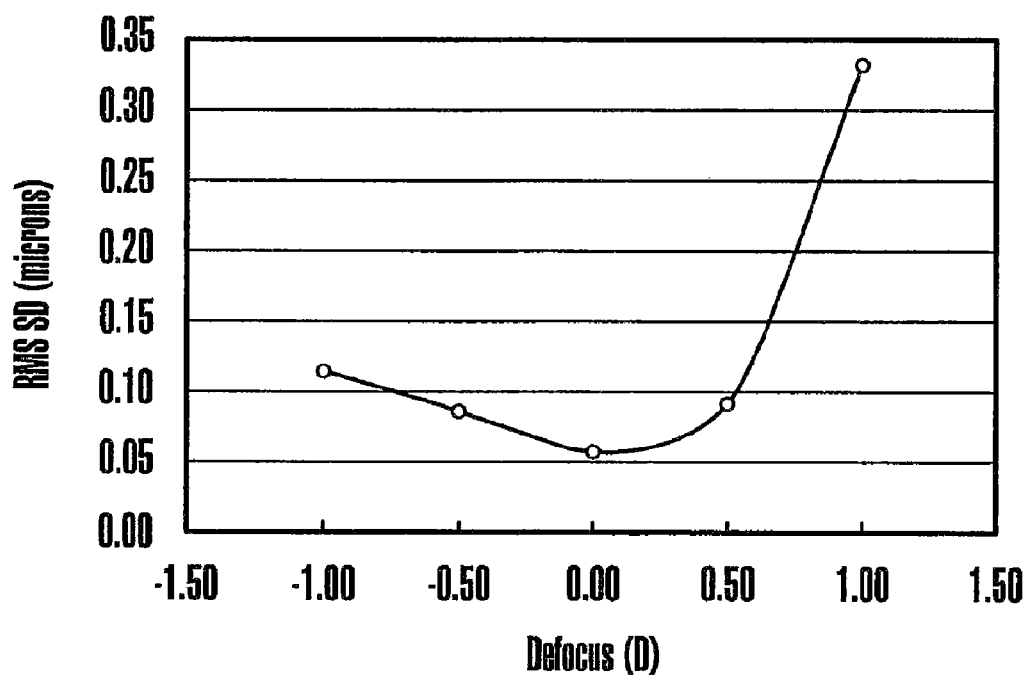
FIG. 3 is an exemplary plot of standard deviation (fluctuation) of the total root means square value (RMS) of the wavefront measurement (in units of microns) versus added defocus power (in units of diopters) with a minimum point of vision fluctuations near 0.35 D.

Accordingly, one embodiment of arriving at subjective refraction using an objective measurement is to measure the spherical equivalent, determine axis, and also measure cylinder. The spherical equivalent may be determined as described above, for example, using a plurality of test lenses or by changing the test lens power via a motorized mechanism in variable focal length compound lens device. Such a lens device, referred to generally as the test lens 58 in FIG. 1, may comprise a combination of positive and negative power lenses with appropriate distance separating the lenses to provide the desired power. In one embodiment, multiple wavefront measurements are made for each lens power, and standard deviation (SD) of the RMS wavefront error values for each lens power may be determined as a measure of the fluctuation of the quality of vision. A minimum point exists when a plot is made of the SD of total RMS wavefront error versus the lens power, provided that the lens power is scanned within a power range that overlaps with the manifest refraction power. Additional details regarding the range and the central point of the scan are presented more below. An example of a plot of the SD of total RMS wavefront error in microns versus the lens power (defocus) in diopters is shown in FIG. 3.

In one embodiment, after the value of the spherical equivalent is determined using the method described above, the cylinder axis can be ascertained using a Jackson Cross Cylinder. Jackson Cross Cylinders are employed by optometrists using phoropters in conventional examinations. In various preferred embodiments, however, no oral or other response from the patient is solicited. Instead, the amplitude of the vision fluctuation is measured as described above while the angle of the Jackson Cross Cylinder is varied. The axis may be obtained from the low value or minimum in a plot of vision fluctuation versus angle. A curve fitting routine may be employed to more precisely determine a low or minimum value.

After the axis is determined, one may introduce a plurality of different values of cylindrical correction into the patient's field-of-view as the patient views a target. The precise cylinder value can be obtained, for example, using vision fluctuation as an indicator of the patient's preference, in a manner as described above, again without soliciting the patient's opinion of his or her quality of vision. This procedure may be repeated for both eyes and the two eyes may be balanced. In this manner, however, the "manifest" or subjective refraction can be determined using "objective" wavefront measurements.

In various preferred embodiments, cylinder may be determined without using a series of cylindrical test lenses (or motorized variable test lens systems that introduce cylinder). These embodiments may preferably employ only spherical test lenses or motorized compound optics configured to provide sphere power change or defocus without the need for cylinder. These embodiment, therefore, offer an advantageous simplification of the measurement apparatus and methods.

These methods for determining cylinder by testing multiple defocus values can be understood by considering the following example of an eye having a refractive error of −3.0 D (sphere) and −1.5 D cylinder at 35 degrees. One skilled in the art will readily recognize the character of this error and understand that this same prescription can also be denoted by −4.5 D of sphere and +1.5 D cylinder at 125 degrees. (As used herein, refractive error of the eye corresponds to the prescription for correcting the eye and is opposite in sign to the corresponding error in the optic of a natural eye.) As is well known, optometrists generally prefer the negative cylinder notation (e.g., −3.0 D and −1.5 D @ 35°), and the medical doctors prefer the positive cylinder notation (e.g., −4.5 D and +1.5 D @ 125°). Both notations, however, represent the exact same refractive error condition.

In this example, the spherical equivalent (SE) of this patient is −3.75 D. The spherical equivalent corresponds to the spherical term plus half of the cylinder term, e.g., −3.0 D+½ (−1.5 D) or alternatively −4.5 D+½ (1.5 D).

In certain embodiments, one may use the wavefront measurements as a starting point to arrive at the estimated values of the spherical equivalent, sphere, cylinder and axis angle. This spherical equivalent value may be chosen as an estimate of the plano defocus position and additional defocus power may be added to the patient's line of sight to search for the subjective manifest refraction. One may prefer to choose to scan the defocus optics values ranging from −1.0 D to +1.0 D centering around the spherical equivalent point. The actual compensating power in this example would therefore be scanned from −3.75 D+(−1.0 D)=−4.75 D to −3.75 D+1.0 D=−2.75 D. If scanning in increments of 0.25 D, the compensating optics will step through −4.75 D, −4.5 D, −4.25 D, . . . −3.0 D, −2.75 D, in a total of 9 steps. Alternatively, a larger or smaller scan range (instead of +1.0 D) and/or larger or smaller step size (instead of 0.25 D) may be employed. Such scanning may be employed to more precisely determine the spherical equivalent values.

An embodiment for a method of determining subjective cylinder value is described as follows. In the example used above, when the compensation or test optics provides −4.5 D defocus correction, the residual refractive error of the patient is +1.5 D pure cylinder at 125 degrees. Likewise when the optics provides compensation of −3.0 D sphere, the patient has a residual error of −1.50 pure cylinder at 35 degrees. A pure cylinder is defined as a refractive error that has no residual sphere component, either in the negative or in the positive cylinder notation of a patient's prescription.

If the patient is presented with a target in which the patient cannot discern error along the direction orthogonal to the axis of the cylinder, then the patient will have perfect vision when compensation equivalent to the sphere component (e.g., −3.0 D or −4.5 D) is provided. In such a case the residual refractive error (−1.5 D or +1.5 D) is pure cylinder; however, this pure cylinder is not discernable because of the special target.

Such a target may comprise a plurality of elongated features such as parallel lines. These plurality of parallel lines are oriented perpendicular (and/or parallel) to the cylinder axis in various preferred embodiments. With proper orientation of the parallel lines, the subject cannot discern the effects of cylindrical error. In one embodiment, a target image such as the one described above is provided by a liquid crystal display (LCD) or other type of graphic display on which various images may be provided and manipulated or altered electronically as desired via a computer and associated software.

Figure 4:
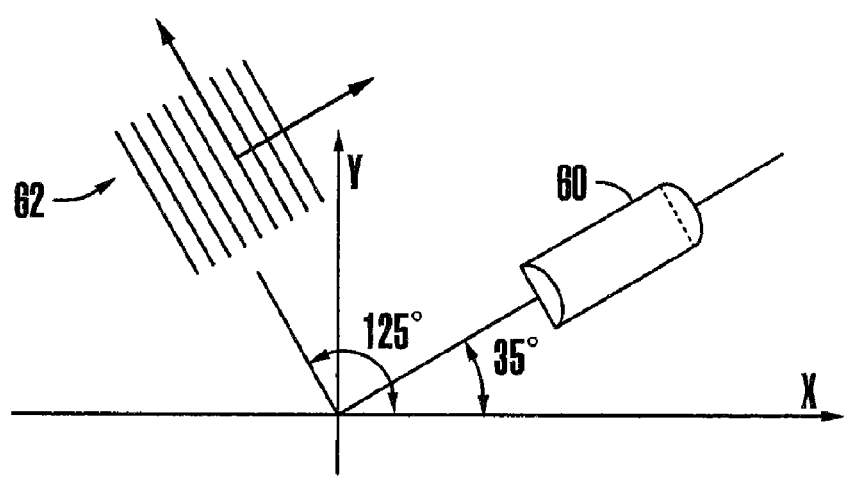
FIG. 4 is a schematic diagram illustrating a suitable orientation of a target comprising a plurality of parallel lines oriented with respect to axis of cylinder for a person's eye for certain methods of measurement of cylinder disclosed herein.

FIG. 4, for example, illustrates a case wherein the patient has a residual prescription of −1.5 D pure cylinder at 35 degree (likewise the optic of the natural eye has a +1.5 D cylinder error). The +1.5 D cylindrical error for the optic of the natural eye is represented in FIG. 4 by a positive cylindrical lens shape 60 having an axis oriented at 35°. A target 62 is also shown with lines oriented exactly at 125 degrees (90 degrees perpendicular to the axis angle). Accordingly, the patient would see a perfectly sharp image of the lines on the target in the case where −3.0 D spherical correction is provided. FIG. 4 illustrates the relative orientation of the cylinder error of the optic of the unaided eye, and the parallel lines oriented for which the patient would see a sharp image of the lines. The line image would remain sharp for other values of cylinder errors as well. Both positive and negative cylinders are possible provided that the cylinder is at 35°, and the length of the parallel lines extends beyond the angle subtended by the view-of-field of the patient.

This drawing in FIG. 4 is schematic. Although the target 62 is depicted as comprising a series of thin lines with wider "white" line spacing, the width of the black and the white lines are preferably equal. The lines need not, however, be black and white nor all the same width or periodicity, although such a target may be preferred. In various preferred embodiments, however, the lines are parallel and have a constant spacing and line width.

With this arrangement, therefore, the method of determining the spherical equivalent (SE) using the objective wavefront measurement, as described in U.S. patent application Ser. No. 10/076,218 and U.S. patent application Ser. No. 10/653,552, can be employed to determine the amplitude of the cylinder component. The relationship between fluctuation in a chosen quality of vision metric versus the added defocus power in the compensating optics, if plotted, may yield a curve similar to the plot shown in FIG. 3. This curve includes a minimum point where the amount of spherical correction that together with the pure cylinder residual refractive error, corresponds to the patient's subjective refraction value. This minimum point can therefore be identified to determine the patient's subjective refraction.

In one exemplary embodiment, a patient's refractive error is first estimated using a wavefront sensor. Multiple measurements may be taken to obtain a more reproducible wavefront-based estimate by averaging and/or other processing of the measurements.

From the series of wavefront measurements, an estimate of the spherical equivalent (SE) is known. Similarly, estimates of the cylinder values for both the positive and negative cylinder notations, and the corresponding axis angle values are also obtained from the wavefront measurement. The axis angle ascertained from wavefront measurements by the wavefront sensor is more repeatable and accurate, and equal or better than that obtained from using a phoropter in a manual manifest refraction procedure. The wavefront based axis angle value may therefore be used as the starting point. With the axis value known, the targets may be accurately rotated to align the parallel lines with a direction such that the patient would see perfect even if he/she still has residual cylinder errors.

Accordingly, a target comprising a plurality of parallel and elongated features such as parallel lines may be presented in place of the typical eye charts for the patient. The target is preferably placed at a distance of between 8-20 feet from the optics 58 (FIG. 1), and the optics 58 are preferably located near the patient's eye, at or near the spectacles plane. The orientation of the target may be set such that the lines extend in a direction orthogonal to the axis value for the negative cylinder notation as shown in FIG. 4. In the example of a patient's prescription of −3.0 D sphere −1.5 D cylinder at 35 degrees, one may search for the subjective cylinder value by scanning through the defocus at −3.0 D. The central value of the scan preferably corresponds to the amount of spherical correction (−3.0 D in this case) that would provide residual refractive error comprising negative pure cylinder. This central value is determined based on the estimated values obtained from the preceding wavefront measurements. The defocus scanning may be performed for values of sphere ranging from +1.0 D above this central value to −1.0 D below this central value to provide a sufficient range to search the minimum point of vision fluctuation. Alternatively, a narrower range of, e.g., ±0.75 D or ±0.5 D, may be used. The step size may also vary. A smaller step size of 0.125 D may be used to fine-tune the search of the minimum point. Also, in some embodiments, the "central" value need not be the center of the range of values tested, although such an approach may be preferred. A value of spherical correction or defocus power, $D_1$, is thereby determined that corresponds to the spherical correction that yields the low or minimum amount of fluctuation.

This process of scanning through a series of values of sphere or defocus correction is repeated with the target rotated by about ±90° to again search for the subjective cylinder value. For the exemplary case of a patient's prescription of −4.5 D sphere +1.5 D cylinder at 125 degrees, the orientation of the target is therefore set such that the lines extend in a direction orthogonal to 125 degrees for the positive cylinder. Preferably, the target is rotated by an amount corresponding to adding or subtracting 90° to keep the angle of rotation within the range of 0-180 degrees. In this case, the central value of the scan preferably corresponds to or near −4.5 D, the amount of spherical or defocus correction that would provide residual refractive error comprising positive pure cylinder. A value of spherical correction or defocus power, $D_2$, is thereby determined that corresponds to the spherical correction that yields the low or minimum amount of fluctuation.

The amplitude of the cylinder in this case can be calculated by subtracting D2 from D1 (D1−D2), and the spherical equivalent of the subjective refraction value is therefore equal to (D1+D2)/2. This method therefore quantifies the SE, cylinder, and axis associated with the patient's refractive error.

Alternatively, the subjective spherical equivalent can be first determined by the method disclosed in U.S. patent application Ser. No. 10/076,218 entitled "Apparatus And Method For Determining Objective Refraction Using Wavefront Sensing," filed Feb. 13, 2002, as well as U.S. patent application Ser. No. 10/653,552, entitled "Apparatus And Method For Determining Subjective Responses Using Objective Characterization Of Vision Based On Wavefront Sensing" filed Sep. 2, 2003. After obtaining the axis value of the patient's eye the subjective sphere value and the cylinder value can be calculated from the spherical equivalent (SE) and one of the D1 or D2 values. In such a case, only one of D1 or D2, not both, is required for the calculation. Sphere is equal to D1, and the cylinder is 2(SE-D1), and in the case of positive cylinder notation, the sphere is D2, and the cylinder is 2(SE-D2).

As discussed above, the target may comprise a series of black and white lines. The widths of these lines may preferably be determined by a spatial frequency, for example, of about 0.5 to 20 minutes of arc. At about 20 feet, the width of the black lines would therefore preferably be in the range of about 0.8 to 32 millimeters (mm). The width may be scaled accordingly if the target is viewed at distances (or simulated distances) other than about 20 feet.

In some preferred embodiments, the line spacing is fixed in periodicity, the white lines and black lines having the same width. Alternatively, the white lines may have a width that is about 2 to 5 times that of the black lines, and vice versa. Size and spacing outside this range are also possible.

In various embodiments, the width of lines is preferably correlated with the design of the measurement sequence. For example, the range of the optics scan may be selected to be between about plus/minus one diopter (+1 D) and centered about an estimated zero point. The line width may be selected so that the patient experiences a change from blurring of the lines when the optics is set at the end points of the scan and becomes clear and sharp as the optics is scanned through the minimum point of vision fluctuation. In this case, for example, an equivalent of 20/20 visual acuity for the line width may be selected. By adding defocus of either +1.0 D or −1.0 D defocus, the 20/20 lines in the Snellen chart would likely be blurred. The preferred line width would then be in the range of between about 0.6 mm to 2.4 mm, preferably at about 1 to 1.4 mm. However, if a smaller range of values, for example, between about +/−0.5 D is used with a similarly finer step size, the line width may be changed to a smaller range of between about 0.3 to 1.2 mm, and preferably in the range of between about 0.4 to 0.8 mm. Such smaller ranges may be used to fine-tune the measurement of the minimum point to obtain more precise values.

Other embodiments of the target may comprise a series of lines that have a plurality of line widths arranged in an orderly or randomized fashion. For example, the smallest width may be 1 d, while other lines may have widths between 1 d and 10 d, where d is a distance. The lines may be arranged in a sequence of first increasing width, then decreasing, like a sinusoid curve. Alternatively, the 1 d line may be next to a 3 d line and so forth, possibly randomized. Other colors may be used and the colors may vary from one line to another in regular or irregular fashion. Other variations are also possible. As mentioned above, in one embodiment, the size and color of the lines or other target image may be varied as desired by providing the target image on a computer program controlled LCD, computer monitor, raster display or any other type of graphic display that is electronically controllable.

Figures 5, 6:
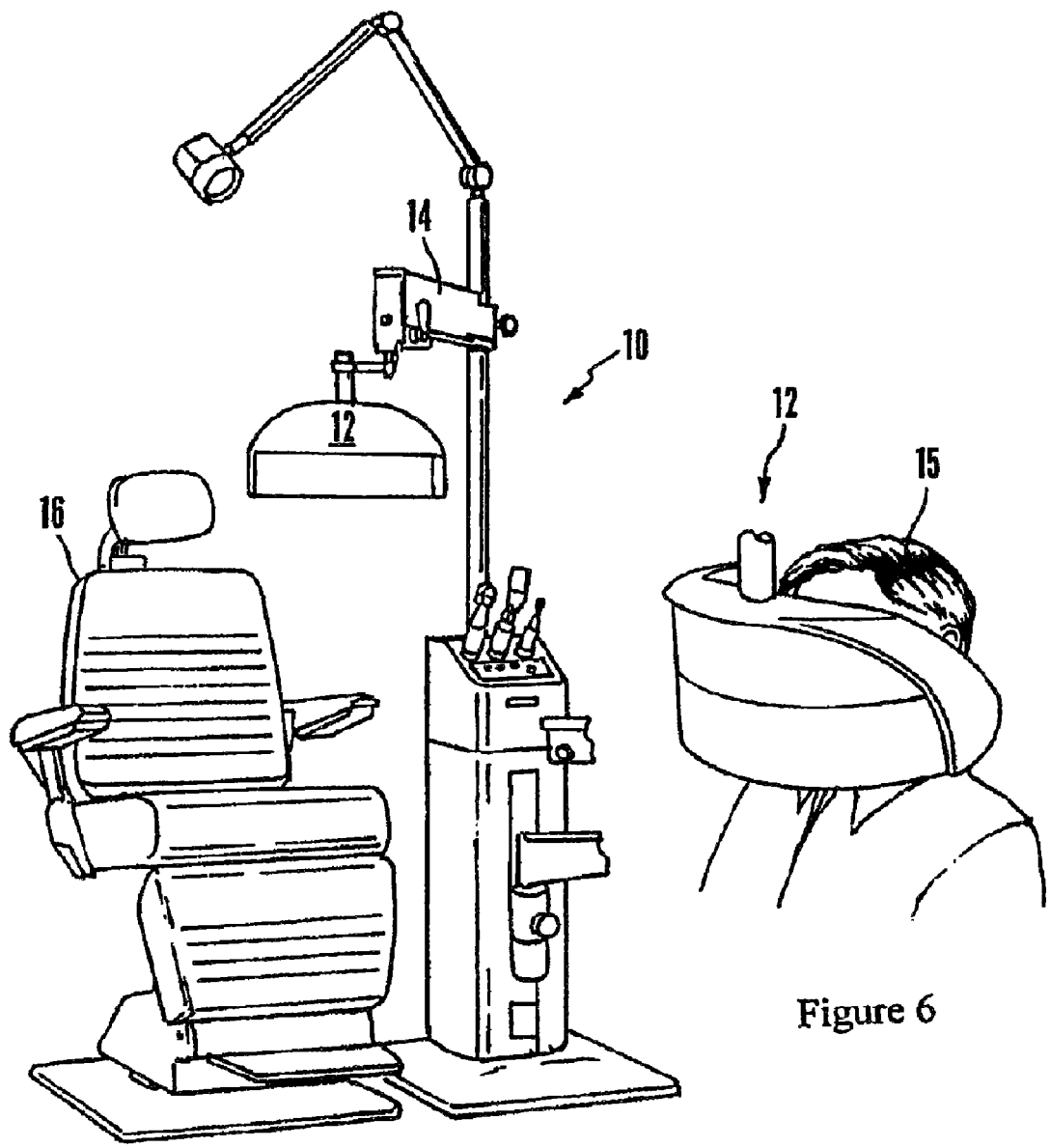
FIGS. 5 and 6 are perspective views of one embodiment of an apparatus for measuring and characterizing a patient's vision.

An exemplary apparatus 10 that can be used to measure subjective refraction, for example, to determine the spherical equivalent and the spherical and/or cylinder components of refraction including axis is shown in FIGS. 5 and 6. Details of such apparatus are also described in U.S. patent application Ser. No. 10/076,218 entitled "Apparatus And Method For Determining Objective Refraction Using Wavefront Sensing," filed Feb. 13, 2002, and U.S. patent application Ser. No. 10/653,552, entitled "Apparatus And Method For Determining Subjective Responses Using Objective Characterization Of Vision Based On Wavefront Sensing" filed Sep. 2, 2003, which are both hereby incorporated herein by reference in their entirety. This apparatus 10 includes a housing 12 that can be mounted on a movable stand 14 for positioning the housing 12 in front of a patient 15 who might sit in an examination chair 16. In certain embodiments, the apparatus can be co-mounted with a conventional phoropter (not shown), in which case the test lenses can be established by the lenses of the conventional phoropter. Other configurations may also be employed.

Figure 7:
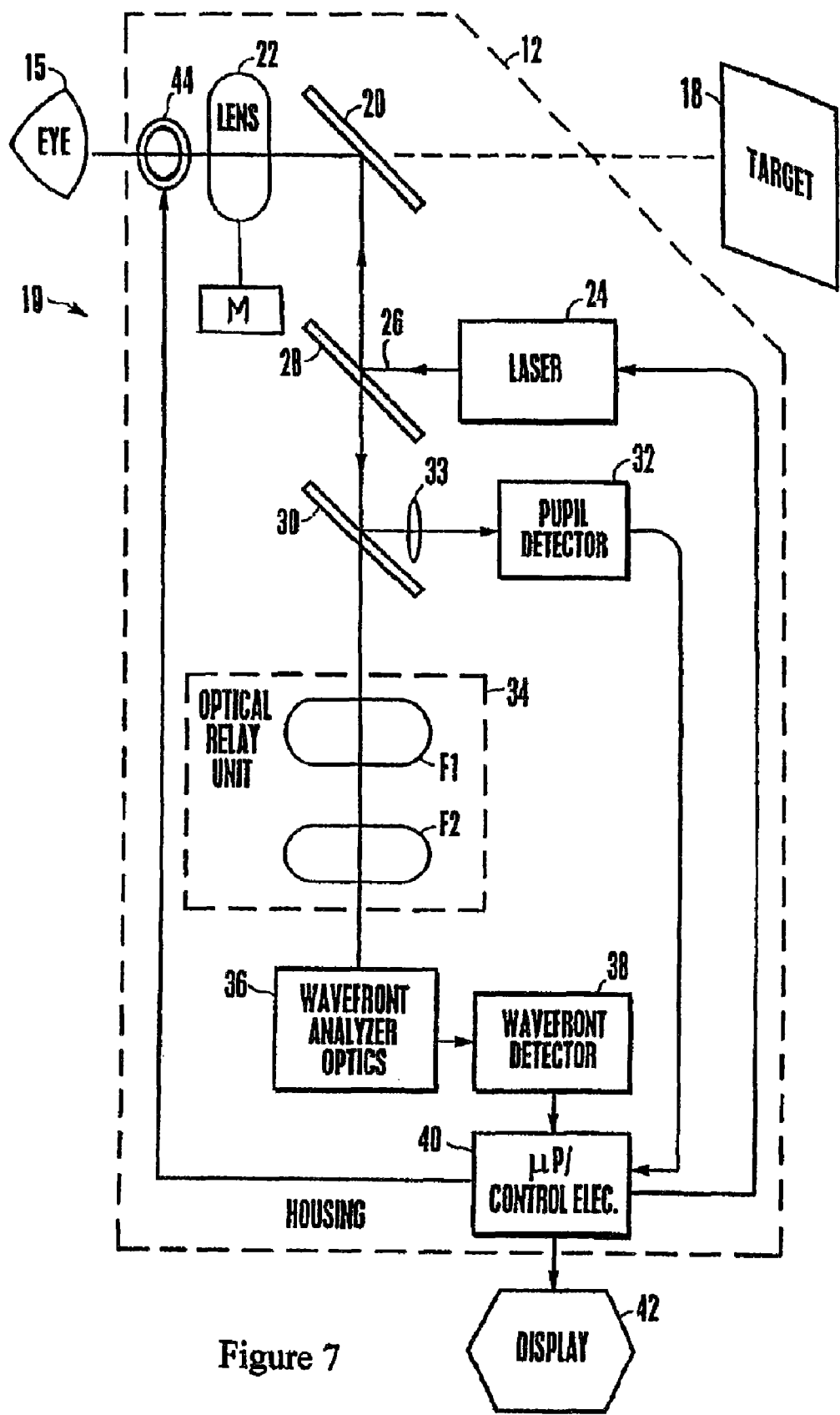
FIG. 7 is a block diagram of the components of one preferred apparatus.

Now referring to FIG. 7, the patient 15 can look through the housing 12 to a target 18, such as but not limited to a Snellen chart or a plurality of parallel lines. The target 18 can be positioned at any appropriate distance from the patient 15, e.g., twenty feet or closer. Preferably, the target 18 is a distance of about 8 to 20 feet from the patient's eye 15. Accordingly, in various preferred embodiments, this target 18 is outside the housing 12. A window in the housing 12 may provide for viewing of a target 18 disposed outside the housing. Internal fixation targets may be used as well in some embodiments. For example, in some embodiments for measuring cylinder, the target 12 comprises a plurality of elongated features such as parallel lines that is rotatably mounted within the housing 12. The target 18 may be rotated based on the axis measured as described above. Optics may create an image of the internal target at a perceived distance, e.g., about 8 to 20 feet, for relaxed viewing by the patient.

In the embodiment shown, the patient looks at the target 18 through a primary beam splitter 20 or other optical element. Interposed in the line of sight of the patient 15 are one or more moveable or changeable (e.g., interchangeable) test lens 22. By "movable" is meant physically movable by hand or computer or electronically-controlled mechanism as indicated as "M" in FIG. 7, such that the lens is selectively interposed in or out of the line of sight of the patient 15. The test lens may also be movable in the sense that a variable focal length lens can be used, with its optical characteristics being variable, such as for example those utilized in various designs of auto refractors. As used herein, the term "changeable" also encompasses "movable", "variable" and "interchangeable" in accordance with the full scope of their ordinary meanings. In certain embodiments for measuring cylinder components as described above, the test lens 22 can include one or more cylindrical lenses configured to provide variable cylinder and/or axis. In various embodiments, for example, a positive and negative lens may be connected to one or more motorized translators to provide adjustable separation therebetween and thus variable defocus. Similarly, positive and negative cylindrical lenses, also motorized, may be controlled to provide variable cylinder and a rotating axis which may be motorized may provide variable axis. Actuators for translation other than motors may also be employed. Adaptive optics may be employed in some embodiments.

The test lens 22 may be disposed in an optical path between the primary beam splitter 20 and the patient's eye 15 as depicted in FIG. 7. Accordingly, in the system shown, the return beam from the lens 22 is detected and analyzed and, hence, the integrated effect on the wavefront introduced by the eye and lens 22 is measured. Alternatively, a system 10 may be used wherein the return beam from the eye can also be analyzed without passing through the lens 22. The test lens 22 may for example be located between the primary beam splitter 20 and the target 18.

As also shown, a light source such as but not limited to a laser 24 generates a light beam 26 that can be directed, in one preferred embodiment, toward a laser beamsplitter 28. The laser beamsplitter 28 reflects the light beam 26 toward the primary beamsplitter 20, which in turn reflects the beam through the test lens 22 and onto the eye of the patient. Note that in certain embodiments, the test lens 22 may be inserted in the optical path between the beamsplitter 20 and the target such that the laser beam 26 does not pass therethrough. Other configurations are readily identifiable by one of ordinary skill in the art.

With reference again to FIG. 7, after reaching the eye 15, the beam 26 is reflected therefrom, back through the lens 22, and is reflected off the primary beamsplitter 20. The beam passes through the laser beamsplitter 28, and a portion of the beam is reflected off a pupil detection beamsplitter 30 toward a pupil light detector 32 through one or more focusing lenses 33, as described more fully below. A portion of the return beam passes through the pupil detection beamsplitter 30 and propagates through an optical relay unit 34, which focuses the beam onto a wavefront analyzer optics 36. The wavefront analyzer optics 36 generates a signal representative of the wavefront of the return beam, and a wavefront detector 38 transforms the signal into an electrical signal for analysis by a processor 40. In one preferred embodiment, the processor 40 can be associated with control electronics for undertaking control of one or more components (e.g., the motor, M, rotatable target, etc.) of the system 10. Also, the processor 40 can generate the visual indications of the patient's vision as corrected by the test lens 22 and can cause the indications to be displayed on a display device 42, such as a video monitor, that can be mounted on the housing 12 or apart therefrom. Suitable displays may include, but not be limited to, numerical and/or graphical representations indicative of the patient's quality of vision, as described more fully below.

If desired, an illumination light 44 can be mounted on the housing 12 and to monitor and adjust the pupil size of the patient 15. The light intensity of the illumination light 44 may be controlled by the processor 40 in response to feedback from the pupil detector 32, which can comprise, e.g., a CCD camera, or reticon detector array to monitor the size and location of the pupil.

As a further improvement to the accuracy of the refraction measurement, the system can also monitor the first Purkinge image, an image formed by reflection at the anterior surface of the cornea of the light beam 26. The position of this image relative to the pupil boundary is an indication of gazing direction of the patient under examination. Such analysis can determine whether the patient is looking at the target, or momentarily drifting off.

In one embodiment, the wavefront analyzer optics 36 may include an array of lenslets arranged as in a Shack-Hartmann wavefront sensor, an example of which can be found in page 37, "Customized Corneal Ablation The Quest for Super Vision" edited by MacRae, et. al. published by Slack Incorporated, 2001, incorporated herein by reference. Various Shack-Hartmann wavefront sensors and processors are available, for example, from commercial vendors such as Wavefront Sciences, in Albuquerque, N. Mex., Zeiss/Humphrey Instruments, in Dublin, Calif., or Bausch and Lomb, in Irvine, Calif. More preferably, the optics 36 can include a periodic diffraction element such as two-dimensional modulation pattern in a Talbot/self-imaging plane based wavefront sensor such as those disclosed in co-pending U.S. patent application Ser. No. 10/014,037, entitled "System And Method For Wavefront Measurement", filed Dec. 10, 2001, and U.S. patent application Ser. No. 10/314,906, entitled "Systems And Methods For Wavefront Measurement", filed Dec. 9, 2002, both of which are incorporated herein by reference in their entireties, which use a self-imaging diffraction principle to detect the wavefront in the return beam. A self-imaging based wavefront sensor is also described in U.S. Provisional Patent Application No. 60/581,127 entitled "Lensometers And Wavefront Sensors And Methods Of Measuring Aberration," filed Jun. 18, 2004, which is hereby incorporated herein by reference in its entirety.

Regardless of the type of wavefront sensor 36 used, the processor 40 preferably calculates the profile of the wavefront of the light returned from the patient's eye, and may quantify the wavefront aberrations including: low order aberrations such as spherical refractive error, cylinder, and axis, as well as higher order aberrations, such as, coma, spherical aberrations and other higher order terms that can be described, for example, by Zernike polynomials.

For input received from the wavefront sensor 40, various figures of merit may be employed to characterize the quality of the patient's vision. For example, the processor 40 may determine the point spread function (PSF) that is derived from using, for instance, the terms of Zernike polynomials, which is in turn derived from the wavefront passing through the wavefront analyzer optics 36. Other figures of merit, for example, modulation transfer functions, may also be employed.

The measurement accuracy can be improved by monitoring the gazing direction of the patient, and the computing device 40 can reject the data points acquired when the patient was not looking at the designated target. Furthermore, the computing device 40 can also accumulate data and perform calculations for average values and standard deviations for selected subsets of measurements.

Figure 2:
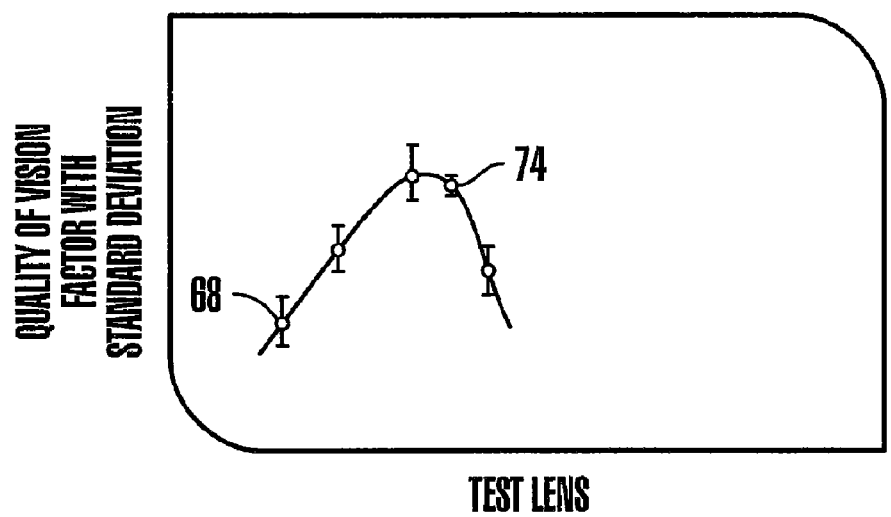
FIG. 2 is a schematic plot of a quality of vision factor (in arbitrary units) versus refractive correction (in arbitrary units) for a variety of test lenses used to determine suitable optical correction for a patient.

FIG. 2, described above, shows a plot of a patient's figure of merit, or the quality of vision factor, QVF such as total RMS values from the wavefront measurement and the standard deviation of the RMS as a measure of the fluctuation of the patient's quality of vision. In this example, five lens powers 22 have been tested and several RMS values (QVF) obtained over a short period for each. Each group of QVF values is plotted along a vertical line 68 on a plot of QVF versus lens, with the length of each error bar line 68 representing the standard deviation of the QVF measurements for that particular lens power and the center of each line representing the mean QVF value. As discussed above, in certain preferred embodiments, the correction can be determined based on a small standard deviation, as indicated by bar 74. For example, the lens corresponding to the bar 74 might be selected because its QVF values had a relatively small standard deviation.

As an alternative, a plot of the standard deviation of RMS wavefront error versus the lens power (defocus) is shown in FIG. 3. In this plot, the chosen scan range covers the point of minimum fluctuation in the quality of vision, which in this case is at 0.35 D. Accordingly, the patient's vision is most stable when a lens with 0.35 D were used to correct the patient's refractive error. Therefore, the exemplary method has arrived at the determination of a refraction point that is also subjectively preferred by the patient.

Determining the variation in the figure of merit preferably involves performing multiple measurements with consecutive measurements separated by a sufficiently long time interval. This time interval is preferably long enough to permit the eye to adjust its focus. Thus, the variation in data points should reflect adjustments made by the eye such as are present when the eye is straining to focus or accommodate. The time period between consecutive measurements is therefore preferably between about 0.1 to 5 seconds, however, values outside this range are also possible.

The above process of measuring indications of the improvement in vision afforded by a particular test lens 22 to the patient 15 can be continued for a plurality of test lens values. When done by the processor 40, the selection of test lens values to be used may be programmed into the processor 40, for example, in accordance with examination strategy and routines described above.

Figure 8:
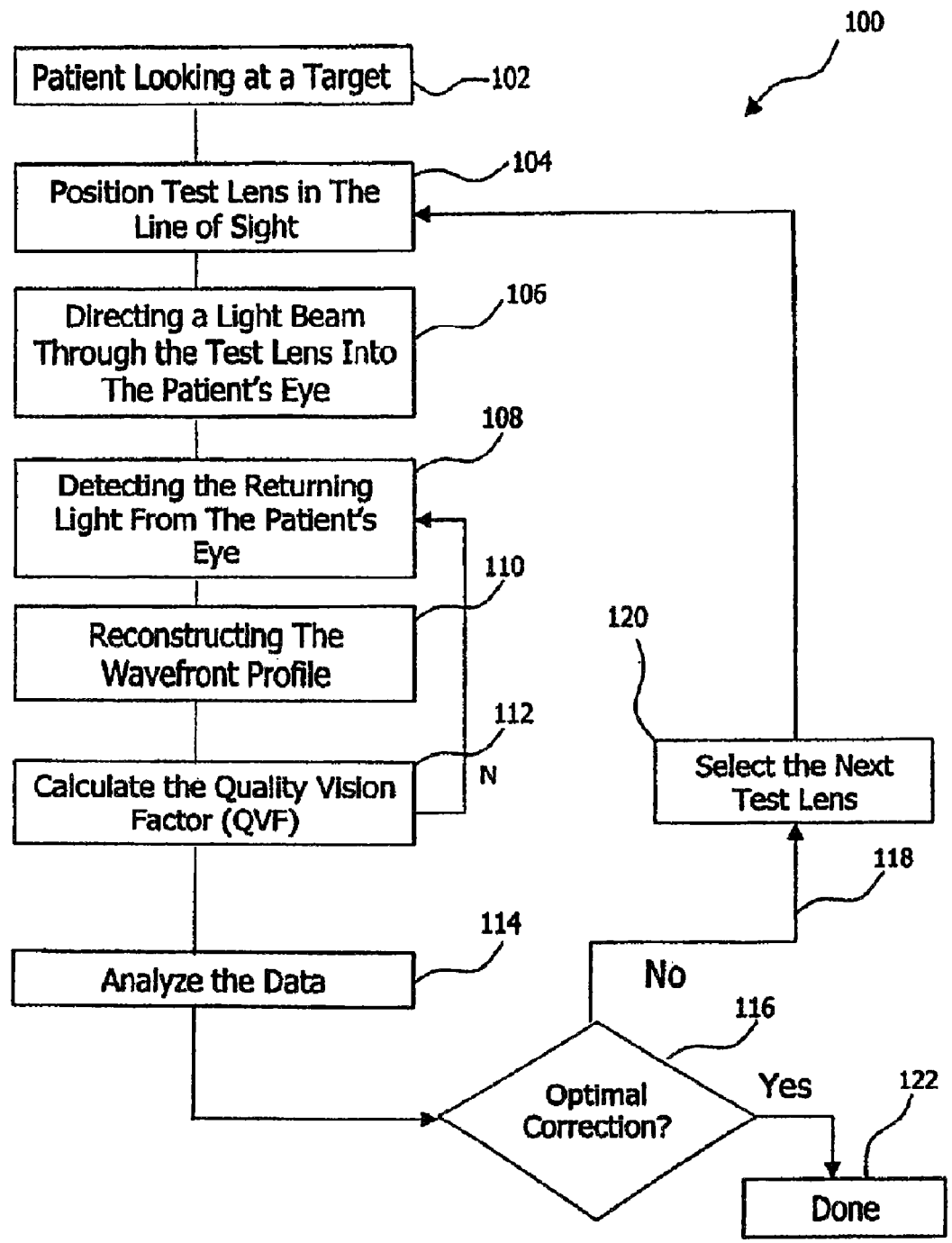
FIG. 8 is a flow chart showing an automatic refraction method described herein.

An exemplary automatic refraction process 100 is depicted in FIG. 8. This process 100 begins with a first step 102 wherein the patient looks at a target. In step 104 a test lens is positioned between the target and the patient's eye, and in the line-of-sight of the patient. A light beam is directed through the test lens and into the patient's eye in step 106. As discussed earlier, an alternative embodiment, the test lens may be positioned outside of the light beam, yet in the line of sight of the patient, positioned between the beam splitter 20 and the target 18 in FIG. 7. In this configuration, the patient's vision is affected by the test lens as he or she is looking at the target, but the wavefront emerging from the patient's eye is directed to the wavefront sensor without passing through the test lens, and thus this wavefront contains both the low order and higher order aberrations of the patient's eye.

In step 108, the light returning from the patient's eye is detected. From this detected light, the wavefront profile may be reconstructed, as shown in step 110. From the reconstructed wavefront profile, the quality of vision factor ("QVF") may be calculated in step 112. "N" wavefront measurements are taken, thereby yielding N wavefront profiles and corresponding QVF values. These successive measurements are taken by returning from step 112 to step 108, in which the returning light is again detected. Steps 108 through 112 are executed "N" times for the test lens (or alternatively N values set by an adjustable lens system). As described above, the "N" measurements are spaced apart in time by a sufficient amount to allow the patient to adjust their focus. For example, this time interval is preferably long enough to permit the muscles in the eye to readjust.

Once "N" measurements have been taken and the QVF for each measurement has been calculated, the QVF measurements such as fluctuation (standard deviation) for that particular test lens are analyzed in step 114. As described above, suitable correction may be determined testing a plurality of test lens or using a test lens having variable optical parameters such as a plurality of lens having variable separation therebetween to provide varying levels of sphere or cylinder. A decision is made in step 116 whether the set of different levels of correction are completed. A wide variety of variations in design and methodology are possible.

In a preferred refraction process, amounts of correction in ¼ diopters increments are used to determine the patient's optical correction. However, in various embodiments of the present invention, more or fewer than the typical number of different correction values may be tested, and the diopter increments can be in ⅛ instead of ¼, or any other value, depending upon the magnitude of correction necessary. Also, as shown in FIG. 8, a number ("N") of measurements of the returning light are performed in steps 108 through 112 to calculate the QVF variation (standard deviation) for the particular level of correction. In some embodiments, for example, 5-20 separate measurements (e.g., "N" equals 5-20) are performed to provide a measure of fluctuation of the QVF. However, more or fewer measurements may be performed depending upon the particular wavefront sensor device used, and the magnitude of correction necessary.

The processor 40 may search for the minimum value among the standard deviation in the data set such as shown in FIG. 2. A relationship similar to the plot in FIG. 3 showing standard deviations versus correction (e.g., spherical, cylinder, axis) can be used in determining the minimum value. Again curve fitting can be employed. The minimum value may be identified for example by detecting the sign change in the slope.

Various processing steps such as described herein that may involve calculations, and other types of activities that can be automated and at least partially implemented using for example computer logic. The methods and processes described herein may illustrate the structure of the logic of various embodiments of the present invention which may be embodied in computer program software. Moreover, those skilled in the art will appreciate that the flow charts and description included herein illustrate the structures of logic elements, such as computer program code elements or electronic logic circuits. Manifestly, various embodiments include a machine component that renders the logic elements in a form that instructs a digital processing apparatus (that is, a computer, controller, processor, etc.) to perform a sequence of function steps corresponding to those shown.

In other words, the logic may be embodied by a computer program that is executed by the processor 40 as a series of computer- or control element-executable instructions. These instructions may reside, for example, in RAM or on a hard drive or optical drive, or the instructions may be stored on magnetic tape, electronic read-only memory, or other appropriate data storage device.

As described above, in various embodiments by measuring fluctuation in quality of vision metrics for patients exposed to different levels of optical correction (e.g., sphere, cylinder and/or axis), objective measurements can be obtained that are indicative of the subjective refraction of a patient. Accordingly, the apparatus and methods described herein advantageously enable quantification of the subjective response of the patient by performing objective measurements, i.e., without relying on the opinion of the patient regarding the quality of their vision, which is required when performing conventional subjective measurements of manifest refraction using a conventional phoropter.

While various embodiments of the present invention have been described above, it should be understood that they have been presented by way of example only, and not of limitation. Thus the breadth and scope of the present invention should not be limited by any of the above-described exemplary embodiments, but should be determined only in accordance with the following claims and their equivalents.

What is claimed is:

1. A method of characterizing cylinder in a person's eye, comprising:
   (a) determining an axis of said eye;
   (b) providing a target image having at least one feature that may be oriented either substantially parallel or substantially perpendicular to said axis;
   (c) selecting a first refractive correction (D1) when the at least one feature is substantially parallel to said axis, wherein selecting a refractive correction comprises:
      (i) repetitively measuring wavefronts emanating from the person's eye for different amounts of refractive correction, said act of repetitively measuring wavefronts comprising performing multiple wavefront measurements using a wavefront sensor;
      (ii) producing a plurality of data sets for the plurality of refractive corrections, respectively, said data sets comprising data points indicative of the quality of vision of the person;
      (iii) calculating the variation in said plurality of data points to provide an objective assessment of the refractive correction for each of said data sets;
      (iv) comparing said variations and selecting an amount of refractive correction based on said comparison;
   (d) selecting a second refractive correction (D2) when the at least one feature is substantially perpendicular to said axis; and
   (e) determining said cylinder of said patient's eye based at least in part on the values of D1 and D2.

2. The method of claim 1, wherein the step of selecting an amount of refractive correction further comprises selecting the refractive correction based on the data set having the least variation in a respective plurality of data points.

3. The method of claim 2 wherein said refractive correction comprises cylinder correction.

4. The method of claim 1 wherein:
   selecting a refractive correction further comprises:
      (v) providing test optics that are changeable to introduce different amounts of refractive correction, wherein said test optics introduce only spherical corrections;
      (vi) repetitively measuring wavefronts emanating from the person's eye, said repetitively measuring comprising:
         (A) adjusting said test optics to provide an amount of refractive correction to be tested; and
         (B) performing multiple wavefront measurement using a wavefront sensor; and
   said method further comprises:
   obtaining a spherical equivalent value for said eye; and
   determining cylinder correction for said eye based on said spherical equivalent value and said first and second refractive corrections.

5. The method of claim 1 wherein D1 is selected based at least in part on a first plurality of data points that exhibit a least amount of variation for a given amount of refractive correction when the target image is oriented substantially parallel to the axis and D2 is selected based at least in part on a second plurality of data points that exhibit a least amount of variation for a given amount of refractive correction when the target image is oriented substantially perpendicular to the axis.

6. An apparatus for automatically determining cylinder correction for a patient's vision, said apparatus comprising:
   a target image having at least one feature that may be oriented either substantially parallel or substantially perpendicular to an axis of an eye of the patient;
   test optics being changeable to provide different amounts of refractive correction;
   an actuator for adjusting the test optics so as to change the amounts of refractive correction, wherein a first refractive correction has at least one feature that is substantially parallel to said axis and a second refractive correction has at least one feature that is substantially perpendicular to said axis;

a light source for directing light into an eye of the patient, said light reflecting from tissue in said eye;

a wavefront sensor for measuring a plurality of wavefronts emanating from the patient's eye for different amounts of refractive correction provided by said test optics; and a processor configured to receive output from said wavefront sensor and to determine a cylinder correction for said patient's eye.

7. The apparatus of claim 6, wherein said wavefront sensor comprises a Talbot based self-imaging wavefront sensor.

8. The apparatus of claim 6, further comprising a computer readable medium having a program of instructions stored thereon for causing said processor to execute method acts comprising:

(a) calculating multiple values of a quality of vision metric indicative of the patient's quality of vision, said multiple values being derived at least in part from multiple wavefront measurements for a given refractive correction; and (b) calculating the variation of the quality of vision metric values for a given refractive correction.

9. The apparatus of claim 8, wherein said method acts comprise:

performing steps (a) and (b) for a plurality of values of refractive correction; and determining said cylinder correction based on one or more refractive corrections that result in reduced variation of said quality of vision metric.

10. A method for determining cylinder correction for a patient's eye, comprising:

(a) providing a target image for viewing by the eye, the image having at least one feature that may be oriented in a desired orientation;

(b) measuring a first plurality of successive wavefronts reflected from the eye while the eye is viewing the target image oriented in a first orientation and subjected to a first refractive correction;

(c) measuring a second plurality of successive wavefronts reflected from the eye while the eye is viewing the target image oriented in the first orientation and subjected to a second refractive correction;

(d) determining a first variation associated with the first plurality of successive wavefront measurements and a second variation associated with the second plurality of successive wavefront measurements;

(e) comparing the first and second variations and selecting either the first refractive correction or the second refractive correction as a first desired refractive correction (D1) based on the comparison;

(f) measuring a third plurality of successive wavefronts reflected from the eye while the eye is viewing the target image oriented in a second orientation and subjected to a third refractive correction;

(g) measuring a fourth plurality of successive wavefronts reflected from the eye while the eye is viewing the target image oriented in the second orientation and subjected to a fourth refractive correction;

(h) determining a third variation associated with the third plurality of successive wavefront measurements and a fourth variation associated with the fourth plurality of successive wavefront measurements; and (i) comparing the third and fourth variations and selecting either the third refractive correction or the fourth refractive correction as a second desired refractive correction (D2) based on the comparison; and (j) calculating a cylinder correction for the patient's eye based at least in part on the selected first desired refractive correction (D1) and second desired refractive correction (D2).

11. The method of claim 10 wherein the first and second refractive corrections are selected to be within a first range of values containing a first spherical equivalent value as a median value and the third and fourth refractive corrections are selected to be within a second range of values containing a second spherical equivalent value as a median value.

12. The method of claim 10 wherein the first and second refractive corrections are selected to be within a first range of values containing a first spherical equivalent value as a median value.

13. The method of claim 10 further comprising obtaining a spherical equivalent value for the eye, wherein the cylinder correction is calculated based on the spherical equivalent value and D1.

14. The method of claim 10 wherein the first refractive correction comprises a first cylinder correction and the second refractive correction comprises a second cylinder correction.

15. The method of claim 10 wherein the first refractive correction comprises a first spherical correction and the second refractive correction comprises a second spherical correction.

* * * * *